United States Patent [19]

Delaney et al.

[11] Patent Number: 4,539,312
[45] Date of Patent: Sep. 3, 1985

[54] USE OF DIAMINO KETONES AS ANALGESIC AGENTS

[75] Inventors: Norma G. Delaney, Princeton; Eric M. Gordon, Pennington, both of N.J.

[73] Assignee: E. R. Squibb & Sons, Inc., Princeton, N.J.

[21] Appl. No.: 629,934

[22] Filed: Jul. 11, 1984

[51] Int. Cl.$^3$ .................... A61K 37/00; C07C 103/52
[52] U.S. Cl. ........................... 514/16; 514/17; 514/18; 514/19; 260/112.5 R
[58] Field of Search .................. 260/112.5 R; 514/16, 514/17, 18, 19

[56] References Cited

FOREIGN PATENT DOCUMENTS 0104041  3/1984  European Pat. Off. ...... 260/112.5 R

OTHER PUBLICATIONS

H. Umezawa et al., J. Antibiotics, vol. 29, p. 97 (1976).
H. Suda et al., J. Antibiotics, vol. 29, p. 100 (1976).
T. Aoyagi et al., J. Antibiotics, vol. 31, p. 636 (1978).
H. Tobe et al., Agric. Biological Chemistry, vol. 43, p. 591 (1979).
"Inhibition of Brain Aminopeptidase by Bestatin and Analogs", G. W. Wagner and J. E. Dixon, J. Neurochem., vol. 37, p. 709 (1980).
"Angiotensin Converting Enzyme Inhibitors: Modifications of a Tripeptide Analogue", R. F. Meyer et al., J. Med. Chem., vol. 25, p. 996 (1982).
T. Aoyagi et al., J. Antibiotics, vol. 36, p. 1572 (1983).
H. Umezawa et al., J. Antibiotics, vol. 36, p. 1576 (1983).

*Primary Examiner*—Delbert R. Phillips
*Attorney, Agent, or Firm*—Lawrence S. Levinson; Donald J. Barrack

[57] ABSTRACT

An enkephalin-degrading aminopeptidase enzyme is inhibited by compounds having the formula

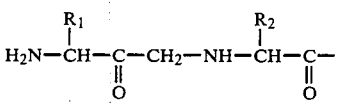

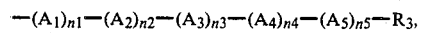

and pharmaceutically acceptable salt thereof, wherein
$R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;
$R_3$ is hydroxy, alkoxy, (substituted alkyl)oxy, arylalkoxy, (heteroaryl)alkoxy or $-NY_1Y_2$, wherein $Y_1$ and $Y_2$ are independently hydrogen, alkyl, aryl, or arylalkyl or $Y_1$ is hydrogen and $Y_2$ is substituted alkyl or (heteroaryl)alkyl;
$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

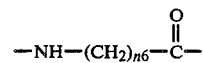

wherein $n_6$ is an integer of 2 to 15;
$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, or prolyl, norleucyl, or norvalyl; and
$n_1$, $n_2$, $n_3$, $n_4$ and $n_5$ each is independently 0 or 1.

15 Claims, No Drawings

USE OF DIAMINO KETONES AS ANALGESIC AGENTS

RELATED APPLICATION

U.S. patent application Ser. No. 515,729, filed July 21, 1983 now U.S. Pat. No. 4514,391, discloses angiotensin converting enzyme inhibitors (hypotensive agents) having the formula

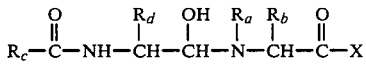

wherein X is an amino (or imino) acid residue, $R_a$ is hydrogen, alkyl, cycloalkyl, or specified substituted alkyl groups; $R_b$ is hydrogen, alkyl, or specified substituted alkyl groups; $R_c$ is specified substituted alkyl groups; and $R_d$ is hydrogen, alkyl or specified substituted alkyl groups which are prepared from the corresponding amino ketone having the formula

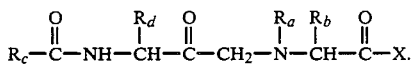

BRIEF DESCRIPTION OF THE INVENTION

Compounds having the formula

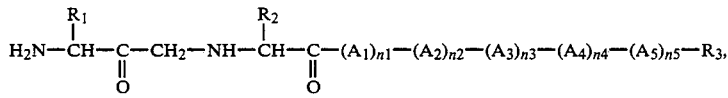

and pharmaceutically acceptable salts thereof, possess inhibitory activity against an enkephalin-degrading aminopeptidase, and can be used as analgesic agents alone, or in conjunction with an enkephalinase inhibitor. This invention is directed to the treatment of pain in a mammalian host by the administration of a compound of formula I. Those compounds of formula I having the formula

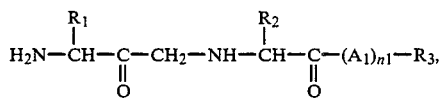

and pharmaceutically acceptable salts thereof, are novel, and as such, form an integral part of this invention.

In formulas I and Ia, and throughout the specification, the symbols are as defined below.

$R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;

$R_3$ is hydroxy, alkoxy, (substituted alkyl)oxy, arylalkoxy, (heteroaryl)alkoxy, or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl;

$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

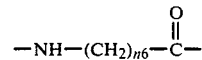

wherein $n_6$ is an integer of 2 to 15;

$A_2$, $A_3$, $A_4$ and $A_5$ each is independently glycyl, alanyl, leucyl, phenylalanyl, arginyl, sarcosyl, seryl, asparagyl, lysyl glutamyl, histidyl, tryptophyl, cysteinyl, methionyl, threonyl, tyrosyl, leucyl, valyl, aspartyl, prolyl, norleucyl, or norvalyl; and $n_1$, $n_2$, $n_3$, $n_4$ and $n_5$ each is independently 0 to 1.

The terms "alkyl" and "alkoxy", as used throughout the specification either individually or as part of a larger group, refer to straight and branched chain groups having 1 to 7 carbon atoms.

The term "halo substituted alkyl", as used throughout the specification either individually or as part of a larger group, refers to alkyl groups in which one, or more, hydrogens have been replaced by chloro, bromo or fluoro groups. Exemplary groups are trifluoromethyl, which is preferred, pentafluoroethyl, 2,2,2-trichloroethyl, chloromethyl and bromomethyl.

The term "cycloalkyl", as used throughout the specification either individually or as part of a larger group, refers to cycloalkyl groups having 3, 4, 5, 6 or 7 carbon atoms.

The term "substituted alkyl", as used throughout the specification, either individually or as part of a larger group, refers to alkyl groups substituted with one, or more (preferably one), hydroxy or $-NY_3Y_4$ groups, wherein $Y_3$ and $Y_4$ are the same or different and each is hydrogen or alkyl, $Y_3$ is hydrogen and $Y_4$ is aryl, or $Y_3$ and $Y_4$ together with the nitrogen atom to which they are attached form a heterocyclic group having the formula

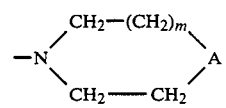

and A is CH—Q, oxygen, or N—Q, Q is hydrogen or alkyl and m is 0 or 1.

The term "heteroaryl", as used throughout the specification either individually or as part of a larger group, refers to 2- or 3-furanyl, 2-or 3-thienyl, 2-, 3- or 4-pyridinyl, 4-imidazolyl and 3-indolyl.

The term "aryl", as used throughout the specification either individually or as part of a larger group, refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

DETAILED DESCRIPTION OF THE INVENTION

The compounds of formula I, and the pharmaceutically acceptable salts thereof, can be administered to a mammalian specie as an analgesic agent due to their ability to inhibit an enkephalin-degrading aminopeptidase.

It is well known that the weak and short-lasting analgesic activity of endogenous enkephalins can be attributed to their rapid inactivation. Enkephalins are metabolized by several hydrolytic enzymes present in the brain: (1) aminopeptidases release the $Tyr^1$ residue, (2) a dipeptidyl aminopeptidase releases the $Tyr^1$-$Gly^2$ residue and (3) two enzymes cleave the penultimate $Gly^3$-$Phe^4$ bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism. The compounds of this invention inhibit the amino peptidase activity and thus act as analgesic agents.

A compound of formula I, or a pharmaceutically acceptable salt thereof, can be administered to patients orally or parenterally in an effective amount within the daily dosage range of about 0.1 to about 25 milligrams of compound per kilogram of patient body weight. Administration can be once daily or in 2 to 4 divided daily doses.

Those compounds of formula I, and pharmaceutically acceptable salts thereof, wherein $R_2$ is a lipophilic sidechain, especially arylalkyl (e.g., benzyl) exhibit inhibitory activity against enkephalin cleaving endopeptidase in addition to the above-described aminopeptidase activity.

The compounds used in the method of this invention can be prepared utilizing as a starting material an amino acid having the formula

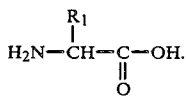

II

The amino group is first protected using, for example, a classical protecting group such as t-butyloxycarbonyl, benzyloxycarbonyl, or o-nitrophenylsulfenyl, and yielding a compound having the formula

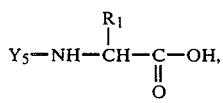

III wherein $Y_5$ is a nitrogen protecting group.

An activated form of an acid of formula III (preferably a mixed anhydride) can be reacted with diazomethane to yield the corresponding diazo compound having the formula

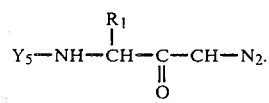

IV

Reaction of a compound of formula IV with hydrogen chloride or hydrogen bromide yields the corresponding compound having the formula

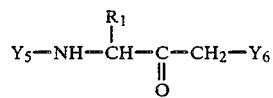

V wherein $Y_6$ is chlorine or bromine.

Reaction of a compound of formula V with an amino acid or peptide having the formula

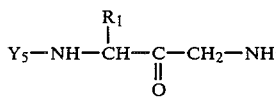

VI yields the corresponding compound

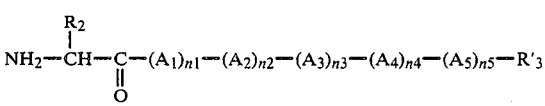

VII

In formulas VI and VII, and throughout the specification, the symbol $R'_3$ is alkoxy, (substituted alkyl)oxy, arylalkoxy, (heteroaryl)alkoxy or $-NY_1Y_2$. The reaction is preferably carried out in the presence of a base such as sodium bicarbonate and sodium iodide as a catalyst.

The products of formula I are obtained from the corresponding compounds of formula VII using standard deprotecting techniques. The particular deprotection reaction used will, of course, depend on the particular $Y_5$ protecting group present.

The compounds of formula I form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonates, (e.g., camphorsulfonate, benzenesulfonate, toluenesulfonate, etc.), citrate, ascorbate, maleate, fumarate, pamoate, acetate, tartrate, salicylate and the like. It is frequently convenient to isolate the compound by forming the acid salt and precipitating in a medium in which it is insoluble.

Products of formula I may have one, or more, asymmetric carbon atoms. If $R_1$ or $R_2$ is other than hydrogen, the carbon atom to which it is attached will be asymmetric. The compounds, therefore, may exist in stereoisomeric forms, and as racemic mixtures thereof. All of these are within the scope of this invention. The above-described syntheses can utilize the racemate or one of the diastereomers as the starting material. When the racemic starting material is used in the synthetic procedure, the stereoisomers obtained in the product can be separated by conventional chromatographic or fractional crystallization techniques. The amino acids designated $A_1$, $A_2$, $A_3$, $A_4$ and $A_5$ may be into L or D configuration.

The following example is a specific embodiment of this invention.

EXAMPLE 1

N-[N-[(S)-3-Amino-2-oxobutyl]-L-phenylalanyl]-L-leucine, dihydrochloride (A) [(S)-3-Diazo-1-methyl-2-oxopropyl]carbamic acid, 1,1-dimethylethyl ester To a vigorously stirred solution of [(t-butyloxy)carbonyl]-L-alanine (15.14 g, 80 mmol) and N-methylmorpholine (8.80 ml, 80 mmol) in 80 ml of dry tetrahydrofuran at −15° C. under argon was added a solution of isobutyl chloroformate (10.37 ml, 80 mmol) in 10 ml tetrahydrofuran, maintaining the reaction temperature below −12° C. After the addition was complete, the reaction mixture was stirred for 14 minutes and then diluted with 250 ml of anhydrous ether (prechilled to −20° C.) and quickly filtered. Approximately one-fourth of the filtrate was transferred to a separatory funnel (the remainder kept chilled) and added rapidly to a gently stirred, chilled (0° C.) solution of diazomethane (160 mmol, generated from 23.54 g of N-methyl-N'-nitro-N-nitrosoguanidine). Additional chilled portions were transferred to the separatory funnel until the entire solution had been added (over approximately 10 minutes). The resulting solution was stirred for 2 hours, warming gradually to room temperature, then purged with nitrogen for 1 hour, washed with chilled half-saturated sodium bicarbonate (2×100 ml) and water (3×50 ml), dried (sodium sulfate) and evaporated to a yellow semi-crystalline residue. Two recrystallizations from ethyl acetate-petroleum ether yielded yellow plates, 10.29 g, melting point 99°–102° C., plus an additional crop of 1.33 g, melting point 97.5√–101° C. A portion was recrystallized once more giving the analytical sample, melting point 102°–103° C.

(B) [(S)-3-Chloro-1-methyl-2-oxopropyl]carbamic acid, 1,1-dimethylethyl ester

Hydrogen chloride gas was slowly bubbled into a chilled (0°–5° C.) solution of [(S)-3-diazo-1-methyl-2-oxopropyl]carbamic acid, 1,1-dimethylethyl ester (9.58 g, 44.9 mmol) in 400 ml of ether until the solution was colorless and nitrogen evolution ceased. The solution was refrigerated for 1 hour, then washed with ice-water (3×50 ml), dried (sodium sulfate) and evaporated yielding 9.87 g of a white crystalline solid, melting point 64°–66.5° C. A portion was recrystallized from ether-petroleum ether giving the analytical sample, melting point 65.5°–67° C.

(C) N-[N-[(S)-3-[[(t-Butyloxy)carbonyl]amino]-2-oxobutyl]-L-phenylalanyl]-L-leucine, t-butyl ester L-Phenylalanyl-L-leucine, t-butyl ester, p-toluenesulfonic acid salt (3.04 g, 6 mmol) was partitioned between saturated sodium bicarbonate (60 ml) and ethyl acetate (100 ml) and the ethyl acetate layer was separated. The aqueous layer was extracted with ethyl acetate (2×25 ml) and the combined ethyl acetate extracts were washed with water (2×20 ml) and brine (25 ml), then dried (sodium sulfate) and evaporated yielding L-phenylalanyl-L-leucine, t-butyl ester (2.18 g) as a colorless oil.

To a stirred solution of L-phenylalanyl-L-leucine, t-butyl ester (6 mmol) in 10 ml of dimethylformamide (under argon) was added a solution of [(S)-3-chloro-1-methyl-2-oxopropyl]- carbamic acid, 1,1-dimethylethyl ester (1.33 g, 6 mmol) in 20 ml of dimethylformamide, followed by sodium iodide (450 mg, 3 mmol) and sodium bicarbonate (504 mg,. 6 mmol). The reaction mixture was allowed to stir for 15 hours, and the solvent was then evaporated (<25° C., vacuum pump). The yellow residue was taken up into ethyl acetate (250 ml) and washed with water (4×25 ml) and brine (25 ml), then dried (sodium sulfate) and evaporated to a yellow residue (3.44 g). This was applied to a column of silica gel (Merck, 230–400 mesh, 250 g) and eluted with hexane-ethyl acetate (1.25:1). Fractions 25–40 (∼30 ml each, homogeneous on TLC) were pooled and concentrated yielding 2.29 g of a colorless oil. Rapid recrystallization from ethyl acetate-hexane afforded 1.61 g of the title compound as a powdery white solid.

(D) N-[N-[(S)-3-Amino-2-oxobutyl]-L-phenylalanyl]-L-leucine, dihydrochloride

A solution of N-[N-[(S)-3-[[(t-butyloxy)- carbonyl]amino]-2-oxobutyl]-L-phenylalanyl]-L-leucine, t-butyl ester (1.61 g, 3.10 mmol) in 40 ml of 1.5 N hydrogen chloride in acetic acid was allowed to stand for 1 hour at room temperature. The solvent was evaporated (<25° C., vacuum pump) and the colorless residue was triturated with ether yielding 1.32 g of a white solid. Analysis by NMR of a small scale reaction run simultaneously showed the reaction to be incomplete. Thus, the solid was again treated with 1.5 N hydrogen chloride in acetic acid (30 ml) for 1 hour, and then worked up as described above affording 1.24 g of a powdery white solid, melting point 131–135° C. (with decomposition beginning ∼120° C.). Analysis Calc'd. for $C_{19}H_{29}N_3O_4 \cdot 2HCl \cdot 0.34$ mol $H_2O$: C, 51.57; H, 7.22; N, 9.50; Cl, 16.02 Found: C, 51.57; H, 7.21; N, 9.23; Cl, 15.97.

What is claimed is:

1. A method of relieving pain in a mammalian host suffering therefrom, which comprises administering an effective amount of a compound having the formula

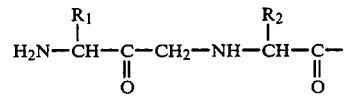

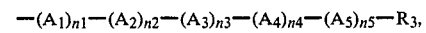

or a pharmaceutically acceptable salt thereof, wherein
$R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;
$R_3$ is hydroxy, alkoxy, (substituted alkyl)oxy, arylalkoxy, (heteroaryl)alkoxy or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl;
$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

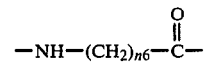

wherein $n_6$ is an integer of 2 to 15;

$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and $n_1$, $n_2$, $n_3$, $n_4$ and $n_5$ each is independently 0 or 1; and wherein the terms "alkyl" and "alkoxy" refer to straight and branched chain groups having 1 to 7 carbon atoms;

the term "halo substituted alkyl" refer to alkyl groups in which one, or more, hydrogens have been replaced by chloro, bromo, or fluoro groups;

the term "cycloalkyl" refers to cycloalkyl groups having 3, 4, 5, 6, or 7 carbon atoms;

the term "substituted alkyl" refers to alkyl groups substituted with one, or more, hydroxy or $-NY_3Y_4$ groups wherein $Y_3$ and $Y_4$ are the same or different and each is hydrogen or alkyl, $Y_3$ is hydrogen and $Y_4$ is aryl, or $Y_3$ and $Y_4$ together with the nitrogen atom to which they are attached form a heterocyclic group having the formula

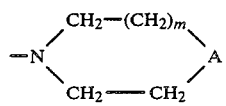

and A is CH—Q, oxygen, or N—Q, Q is hydrogen or alkyl and m is 0 or 1;

the term "heteroaryl" refers to 2- or 3-furanyl, 2- or 3-thienyl, 2-, 3- or 4-pyridinyl, 4-imidazolyl and 3-indolyl; and the term "aryl" refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

2. A method in accordance with claim 1 wherein the compound has the formula

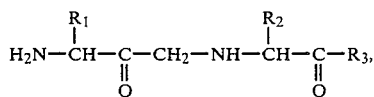

or a pharmaceutically acceptable salt thereof.

3. A method in accordance with claim 1 wherein the compound has the formula

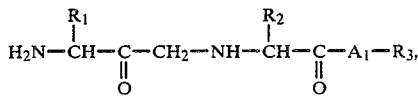

or a pharmaceutically acceptable salt thereof.

4. A method in accordance with claim 1 wherein the compound has the formula

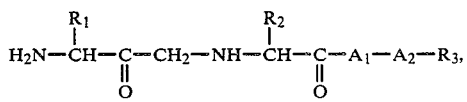

or a pharmaceutically acceptable salt thereof.

5. A method in accordance with claim 1 wherein the compound has the formula

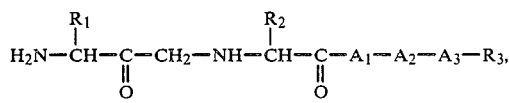

or a pharmaceutically acceptable salt thereof.

6. A method in accordance with claim 1 wherein the compound has the formula

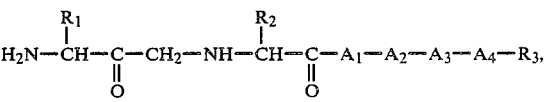

or a pharmaceutically acceptable salt thereof.

7. A method in accordance with claim 1 wherein the compound has the formula

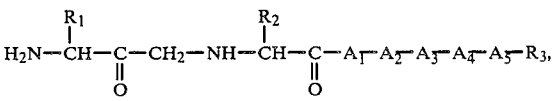

or a pharmaceutically acceptable salt thereof.

8. A method in accordance with claim 1 wherein one of $R_1$ and $R_2$ is phenylmethyl and the other is methyl.

9. A method in accordance with claim 1 wherein each of $R_1$ and $R_2$ is phenylmethyl.

10. A method in accordance with claim 1 wherein each of $R_1$ and $R_2$ is isobutyl.

11. A method in accordance with claim 1 wherein one of $R_1$ and $R_2$ is phenylmethyl and the other is isobutyl.

12. A method in accordance with claim 1 wherein $R_3$ is hydroxy.

13. A method in accordance with claim 1 wherein $R_3$ is alkoxy.

14. A method in accordance with claim 1 wherein $R_3$ is arylalkoxy.

15. A method in accordance with claim 1 wherein $R_3$ is $NY_1Y_2$.

* * * * *